United States Patent
Shepley

Patent Number: 6,024,281
Date of Patent: *Feb. 15, 2000

[54] NUTRITIONAL INFORMATION SYSTEM FOR SHOPPERS

[76] Inventor: Kenneth James Shepley, 140 Golf House Rd., Haverford, Pa. 19041

[*] Notice: This patent is subject to a terminal disclaimer.

[21] Appl. No.: 08/934,697

[22] Filed: Sep. 22, 1997

Related U.S. Application Data

[63] Continuation-in-part of application No. 07/413,275, Sep. 27, 1989, abandoned, application No. 08/046,496, Apr. 13, 1993, Pat. No. 5,478,989, and application No. 08/484,794, Jun. 7, 1995, Pat. No. 5,841,115.

[51] Int. Cl.[7] ........................................................ G06F 17/00
[52] U.S. Cl. .......................... 235/375; 235/380; 235/383
[58] Field of Search .................................. 235/375, 380, 235/383; 364/709.03, 709.02

[56] References Cited

U.S. PATENT DOCUMENTS

| | | | |
|---|---|---|---|
| 4,244,020 | 1/1981 | Ratcliff | 364/413 |
| 4,686,624 | 8/1987 | Blum et al. | 364/415 |
| 4,796,182 | 1/1989 | Duboff | 364/412.29 |
| 4,855,945 | 8/1989 | Sakai | 364/709.02 |
| 4,891,756 | 1/1990 | Williams, III | 364/413.29 |
| 4,894,793 | 1/1990 | Ikemoto et al. | 364/709.03 |
| 4,911,256 | 3/1990 | Attikiouzel | 177/25.16 |
| 4,954,954 | 9/1990 | Madsen et al. | 364/413.29 |
| 5,233,520 | 8/1993 | Kretsch et al. | 364/413.29 |
| 5,478,989 | 12/1995 | Shepley | 235/375 |
| 5,841,115 | 11/1998 | Shepley | 235/375 |

*Primary Examiner*—Donald Hajec
*Assistant Examiner*—Douglas X. Rodriguez

[57] ABSTRACT

A method for providing personalized nutrition information to an individual comprising the following steps: (a) inputting personal data relating to an individual; (b) inputting data identifying at least one food product which the individual intends to purchase or consume; (c) accessing prestored information relating to the at least one food product which the individual intends to purchase or consume; (d) generating and outputting information about the at least one food product which the individual intends to purchase or consume pertinent to the input personal data.

20 Claims, 3 Drawing Sheets

NUTRITIONAL INFORMATION SYSTEM FOR SHOPPERS

CLAIM OF PRIORITY

This application is a continuation-in-part of U.S. Ser. No. 07/413,275 filed Sep. 27, 1989, now abandoned, and U.S. Ser. No. 08/046,496, filed Apr. 13, 1993, now U.S. Pat. No. 5,478,989, and U.S. Ser. No. 08/484,794, filed Jun. 7, 1995, now U.S. Pat. No. 5,841,115.

FIELD OF THE INVENTION

The present invention is directed to apparatus and methods for outputting and processing nutritional information. In particular, the present invention is directed to novel methods and apparatus for providing nutritional information for specific individuals.

BACKGROUND OF THE INVENTION

It has been established that several problems are seriously hampering advancements in the field of human nutrition:

A. Although consumers want to eat healthfully, they are having difficulty understanding nutrition information, comparing and selecting food products and figuring out which nutrition claims are really true. They need a convenient source of information other than manufacturers' advertisements.

B. The United States has been unable to meet its goal of providing routine nutrition education and counseling to the consumer through doctors and other health professionals.

C. Researchers are having difficulty collecting accurate data on the nutritional practices and status of consumers using current nutritional assessment methodologies. These problems are further described below:

A. The Problems of Consumers Making Informed Food Choices:

Today's grocery shoppers still have trouble selecting nutritionally desirable foods. Recent surveys show that consumer knowledge of general nutrition is at peak. However, they are not effectively translating this increased level of awareness into improved dietary habits.

Misleading health claims and advertising, confusing food labels and time constraints while shopping in the supermarket contribute to making brand-name food selections difficult. Studies show that consumers desire to buy food based on sound nutrition recommendations.

Government agencies, the scientific community, industry and consumer groups are striving to develop regulations and education programs to improve the situation. For example, supermarkets have devised shelf-labeling systems to draw attention to nutritionally desirable foods. These attempts, however, usually achieve only marginal success. The Nutrition Labeling and Education Act of 1990 addresses some difficulties consumers face when trying to make informed food choices, such as standardizing the nutrition benefits of foods. However, to make proper selections, consumers will still need to interpret and compare nutrition information from many food items at once, in a busy environment.

B. The Problem of Providing Nutrition Education through Physicians:

In 1980, the U.S. Department of Health and Human Services outlined national health goals to be achieved by 1990. They recommended that doctors and health professionals offer nutrition education and counseling during routine office visits. Doctor's offices are a desirable place to provide nutrition education, but the health-care profession has only partially met this goal. The United States medical system is under severe pressure to continue to improve the quality of medical care, while containing costs. While doctors make dietary recommendations in the treatment of disease, they do not routinely provide preventive counseling. Health-care professionals are unable to provide nutrition education and counseling because it is simply too time-consuming. Though most consumers get their nutrition information from magazines and books, they still consider physicians to be the most reliable source for this information. Therefore, it is logical for doctors to provide nutrition education and counseling during routine health-care visits. However, an effective way to execute this goal is missing.

C. Problems of Current Nutritional Assessment Methodologies:

Although researchers have made correlations between diet and disease on the population level (epidemiologically), it has sometimes been difficult to observe these associations on the individual level. Part of the cause for this are the limited methods used to assess the adequacy of a particular individual's nutritional intake.

Researchers and nutritionists usually measure dietary intake by one of three methods: food diary, diet recall, or diet history. The problem with food diaries is poor compliance. It is simply too hard for subjects to record and describe the consumption of every single food. Accurate diaries require the amounts, methods of cooking and times of consumption for each food. The problem with the diet recall and diet history methods is reporting inaccuracies. For most people it is difficult to remember everything they ate, how it was prepared, et cetera. Not only are studies using these methods expensive and time-consuming, they are subject to error.

There have been prior art devices and methods for generating and retrieving computer stored information pertaining to retail merchandise and food. U.S. Pat. No. 4,780,599 discloses an apparatus for retrieving stored information about various items. While the system disclosed in U.S. Pat. No. 4,780,599 discloses information about food products, it does not provide information pertinent to the individual health and diet needs of individual consumers. Prestored computer software data has similarly been used for tracking inventory, see U.S. Pat. No. 4,180,204, and for obtaining and storing data pertinent to customer demographics. None of these prior art systems have been directed toward the use of a computerized system which can be used to determine and match the nutritional requirements of an individual consumer with particular food items and products.

None of these prior art systems utilize a nutritional database comprised of a comprehensive list of foods and have unique nutrition information specific to each and every food. Typically, many foods such as whole wheat breads are frequently grouped together and considered nutritionally identical in studies, when in fact this may not be the case. Errors of this type are inherent to prior art systems. It would be desirable to provide a computerized system which can match the nutritional requirements and preferences of an individual with specific items of food. It would further be desirable to provide a computerized system for generating and correlating individual data regarding nutritional intake and status.

These and other objectives and desires are achieved through the present invention as set forth in the summary and detailed description which follow.

Dietary factors have been implicated in the etiology of diseases such as coronary heart disease and cancer. The elucidation of such relationships, however, has many times proved difficult. In the case of cancer for instance, preliminary correlations based on the results of human epidemiological and experimental animal studies frequently fail to be verified when studied at the level of the individual. Failure of existing nutritional assessment methodologies to provide sufficiently accurate and precise nutrient intake data have been indicated as one of the causes of this problem.

Estimations of dietary intake data used in epidemiologic studies are generally obtained utilizing food diary, diet recall, or diet history methods. Completion of food diaries on a meal-by-meal basis by study subjects is usually the method to which others are compared. More detailed data are available from food diaries since methods of cooking, portion sizes, and exact ingredients used in mixed foods are obtained. Criticisms of this method include the need for well-informed, compliant study participants, which may introduce a bias and behavior modification by study participants during the self-observation period. Other drawbacks include high data analysis costs, and the significant time and energy required by participants to complete the diaries. The minimum sampling time required to estimate intake of various nutrients using this method varies between one and seven days and depends on the sample population size.

Another widely accepted method of assessing nutrient intake is the diet recall. Here, study participants describe their recent food consumption to a trained interviewer. Popular sampling times for diet recalls include 24 hours and seven days. Diet recalls are subject to error due to inaccurate memories of study subjects. This method is generally used to assess the mean intake of groups rather than the intake of individuals.

The third main form of dietary assessment is the diet history. This method usually consists of study participants filling out food frequency questionnaires or being interviewed to determine food intake frequency over some period in the past. In contrast to recall methods, food histories attempt to assess nutrient intake patterns that have occurred further in the past. Since this method depends on the long-term memory recall by the participant, it is regarded as the least accurate. It has been used to assess the past dietary intake of patients currently suffering from cancer to gain insight about the etiology of their disease.

Variations of these three primary methods also exist. Some of these include personal-, telephone-, and mail-assisted reporting, with retrospective and prospective variations of each. Other methods of assessing dietary intake include the duplicate portion sampling technique and biochemical markers. The duplicate food collection method, where study subjects collect separate aliquots of their food for laboratory analysis, is unpopular due the demand put on study participants in order to comply. It has also been shown to be subject to error. Biochemical markers exist for certain nutrients including ascorbate, carotene, vitamin E, riboflavin, folacin, selenium, cholesterol, fatty acids, and animal protein. These types of assays are not available for most other nutrients and are also subject to limitations and errors of their own.

Most of these methods usually convert food consumption information into nutrient intake data via the coding of various foods for entry into computer programs. This involves assigning foods an alphanumeric code looked up from reference tables. The coding process itself is prone to error, since foods may be categorized differently by different people. This step is also costly and time consuming. Variations in the nutrient databases used to define the nutrient composition of foods pose another problem in assessing data. Database error may be due to the nutrient assay methodology that is used to generate the food composition data. Once nutritional intake data is coded, various existing software programs may be utilized to analyze nutrient intake.

The high degree of variability existing in current nutritional intake methodologies has sometimes produced conflicting results. One of the main causes of this problem is the lack of a "gold standard" method that could be used to assess the validity of the methods that are actually used. Current validations of nutritional assessment methodologies rely heavily on reproducibility and cross reference studies. This leaves a strong need for the further refinement of nutritional assessment methodology. A need also exists for lay individuals to be able to make better assessments of their own nutritional status.

In 1980, the U.S. Department of Health and Human Services published specific goals for 1990 in "Promoting health/preventing disease: Objectives for the nation." The Food and Drug Administration was designated as the lead PHS agency in charge of implementing policies for improved nutrition. The PHS indicated that implementation of these goals would require nationwide public and private support.

Specific nutritional objectives for 1990 included requirements that routine professional health-care visits include nutrition education and counseling. Other objectives included decreases in the population's mean serum cholesterol values and increased awareness concerning dietary factors and disease. Mid-course evaluation of the progress on reaching these goals conducted by PHS indicated that several objectives were unlikely to be reached. The inclusion of nutrition education and counseling in all routine health contacts were among these.

Recent market surveys show that consumer knowledge of nutrition is at a peak. This high level of nutrition awareness, however, is not being used effectively to make improvements in eating behavior. Consumers are confused about which food choices are better for them on a brand-name level. It has been shown that consumers want this information. Government agencies, scientific associations, private industry and consumer groups are all striving to develop programs and regulations to improve this situation.

The Nutrition Labeling and Education Act of 1990 addresses many of the difficulties that consumers face when making informed food purchases. However, it still remains up to the consumer to sift through possible misleading health claims, other advertising influences and complicated food label information to make a wise choice. Additional time constraints compound the problem for the average shopper.

SUMMARY OF THE INVENTION

The present invention is directed to an apparatus and method for providing personalized nutritional information to consumers in a simplified manner. In a preferred embodiment, the method of the present invention comprises the following steps: inputting personal data relating to an individual; inputting data identifying the food products which the individual intends to purchase or consume; accessing prestored information relating to the food products which the individual intends to purchase or consume; outputting nutritional information pertinent to the individual's personal data.

In more preferred embodiments, the method of the present invention comprises the following steps: inputting personal data relating to an individual by means of a magnetic data entry card; inputting data identifying the food products which the individual intends to purchase or consume via a keypad entry device; accessing information prestored in an electronic memory device relating to the food products which the individual intends to purchase or consume; outputting nutritional information pertinent to the input personal data.

In yet a further embodiment, the present invention is directed to an apparatus for generating personalized nutritional data information comprising; means for inputting personal data relating to an individual; means for inputting data identifying the food products which an individual intends to purchase or consume; processor means under the control of a prestored computer program for correlating the individual data with prestored nutritional data pertinent to the food products which the individual intends to purchase or consume; and means for outputting nutritional information to the individual relating to the personal data of the individual and the purchase or consumption of the food products. These and other advantages of, the present invention will become apparent from the detailed description which follows.

DETAILED DESCRIPTION OF THE INVENTION

The present invention is described with reference to the enclosed Figures wherein the same numbers are utilized where appropriate. In general, the present invention discloses and is directed to a computerized method and system for providing personalized nutritional information to consumers in a simplified manner. The computerized apparatus and method correlate individual personal data such as age, height, weight, medical conditions, nutritional preferences and demographic data, with the desired food products which the individual seeks to purchase or consume, or has purchased or consumed. Specific nutritional information is then provided to the individual. Specifically, an individualized output is generated which contains information about the nutritional adequacy of food choices, nutrient intake status, recommendations for diet improvement and optional food choices.

Figure 1:
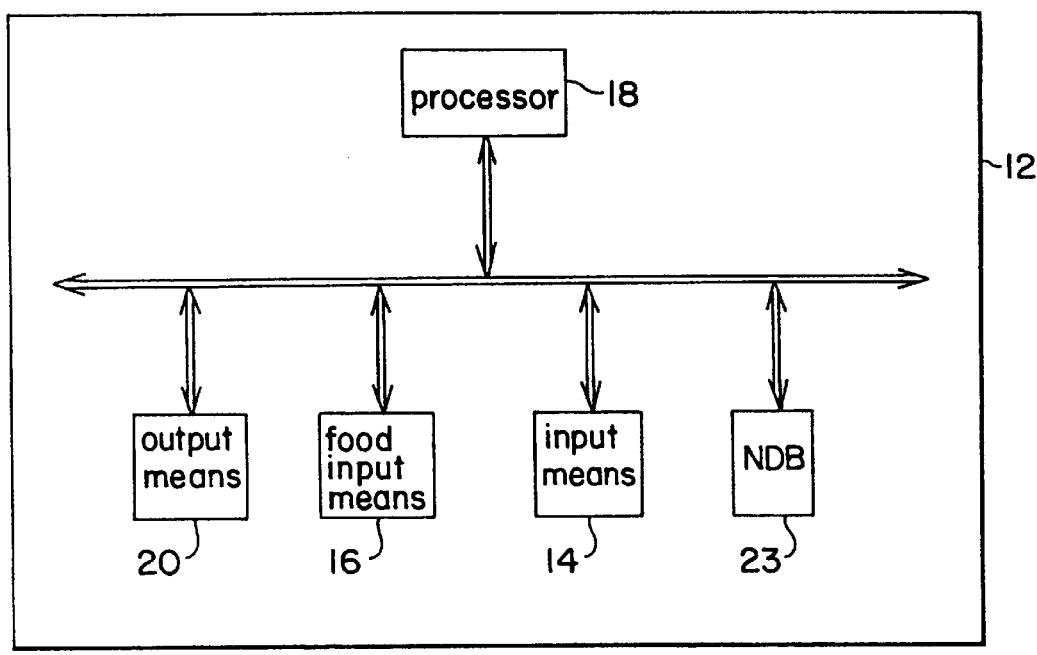
FIG. 1 is a block diagram of a nutritional database access and information system.

Referring to FIG. 1, a block diagram of an initial embodiment of an apparatus 10 for generating personalized nutritional data information is disclosed. In a preferred embodiment, the system 10 comprises a support base 12 and means 14 for inputting personal data relating to an individual. Typically, the support base 12 will be located at an accessible location in a store or market. In the preferred embodiment, means 14 may comprise a magnetic card reader, keypad entry device, touch screen entry system, barcode reader or other well known system for data entry.

In a preferred embodiment, the particular data input regarding the individual may include: the individual's age; the weight of the individual; the gender of the individual; the existence of dietary regulated conditions such as high cholesterol level, high tri-glyceride level, diabetes, hyperglycemia; and the existence of medical conditions such as heart disease, cancer and kidney disease. This data may be previously encoded onto a magnetically striped card and read by a magnetic card reader associated with the system. In the case of a keypad entry system, the user will, in a typical situation, be prompted by queries appearing on a CRT monitor.

Figure 3:
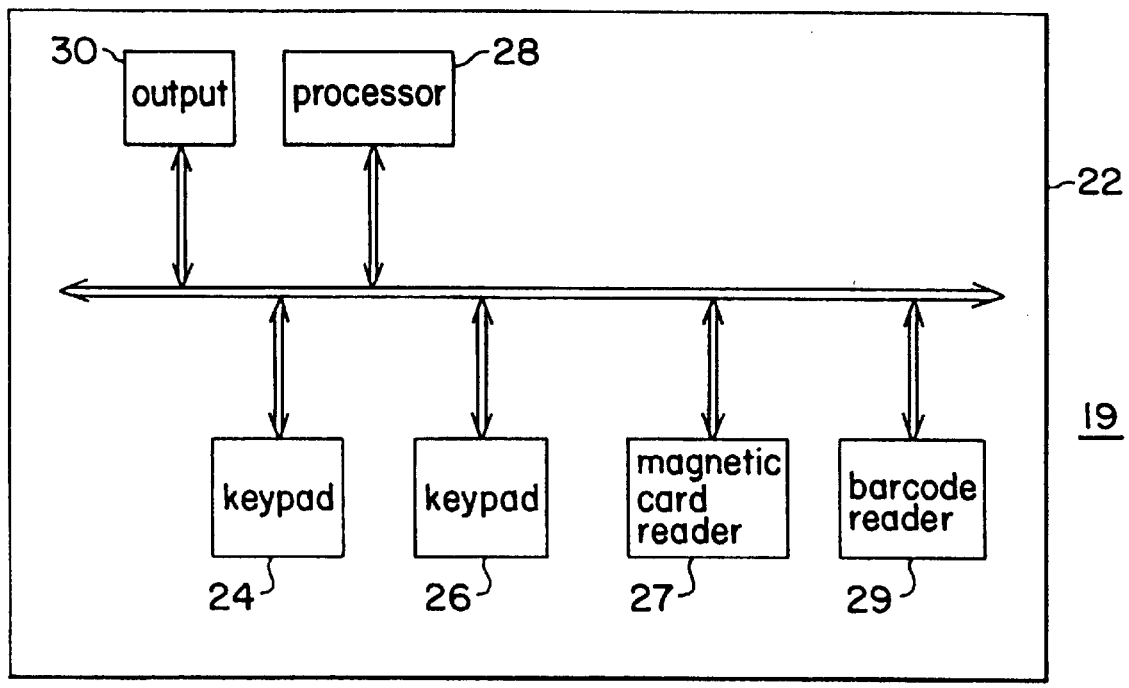
FIG. 3 is a block diagram of a preferred nutritional database access and information system in the form of a kiosk.

The system 10 further provides means 16 for inputting data which identifies at least one food product the individual intends to purchase or consume. Means 16 may also comprise a key pad entry system or touch activated screen input mechanism. Means 16 is utilized by the individual customer to input the various foods and items which the customer intends to purchase or consume. The individual may key in either the brand name of the product or food to be purchased or consumed. With the aid of a barcode reader 29, as shown in FIG. 3, the customer may read in the barcode of the package or processed food good.

The system 10 includes processor means 18 under the control of a prestored computer program. The processor, which is conventional, may comprise an Intel 8086, 80286, 80386, or 80486 processor, Motorola 68000 series processor, or equivalent processor. The processor 18 correlates the personal data input by the individual with prestored nutritional data pertinent to the food product which the individual intends to purchase pursuant to a prestored computer program.

This information is stored in a relational nutritional database (NDB) to be described in greater detail below. The relational database is stored in a large capacity RAM or other large storage medium 23. Finally, in the preferred embodiment, means 20 for outputting information to the individual pertinent to the food product and the personal data of the individual is provided. Means 20 may comprise a CRT monitor, printer or audible message speaker.

The correlated data output will include information and/or recommendations regarding the particular food choices of the individual. For example, if an individual is a diabetic, the system will inform him or her whether any of the chosen foods contain sugars or glucose. The system can be utilized to provide a variety of nutritional information.

FIG. 3 illustrates a more preferred embodiment comprising a free standing or hand-held apparatus for generating personalized nutritional data information. The disclosed system 19 comprises a housing 22 which supports the apparatus. The housing 22, in a preferred embodiment, may comprise a kiosk, check-out counter or hand-held unit having a first keypad entry means 24 for inputting personal data relating to an individual and second keypad entry means 26 for inputting data identifying desired food products which said individual intends to purchase. This embodiment, alternatively, may utilize a magnetic card reader 27 or barcode reader 29 for data input.

This embodiment also includes processor means 28 under the control of a prestored computer program for correlating the personal data with prestored nutritional data pertinent in an NDB to the one food product which the individual intends to purchase or consume. An output means 30 such as a printer or CRT monitor, outputs information to the individual pertinent to the food products to be chosen and the personal data of the individual.

Figure 4A:
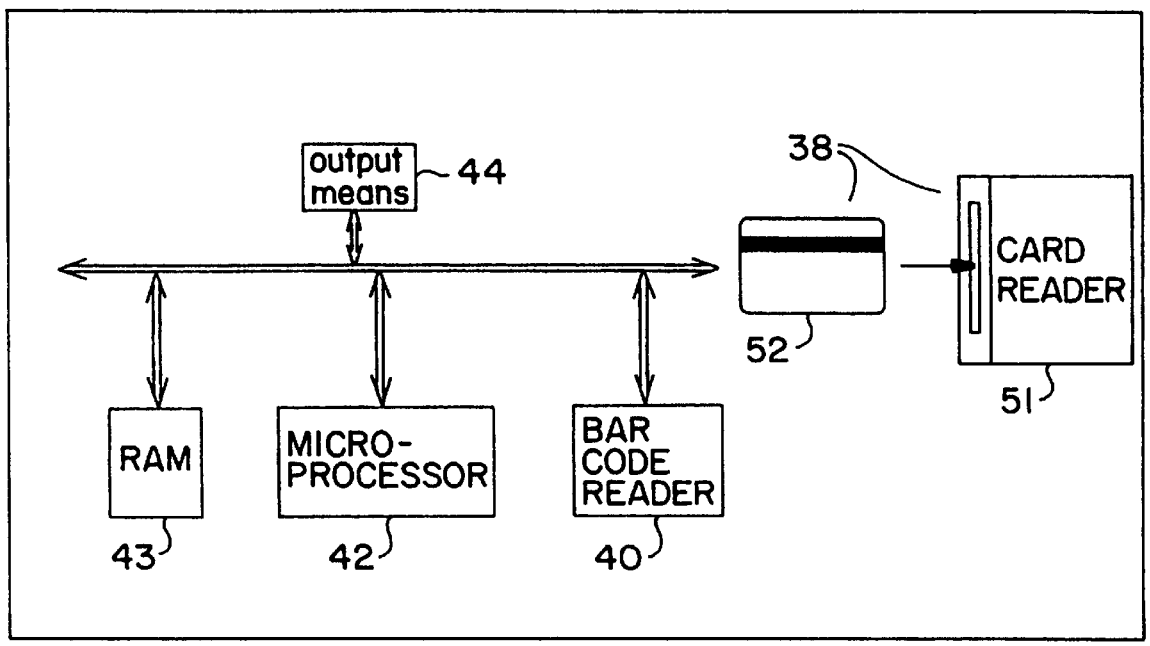
FIG. 4A is an isolated view of the nutritional database access information system of FIG. 4.
Figure 4:
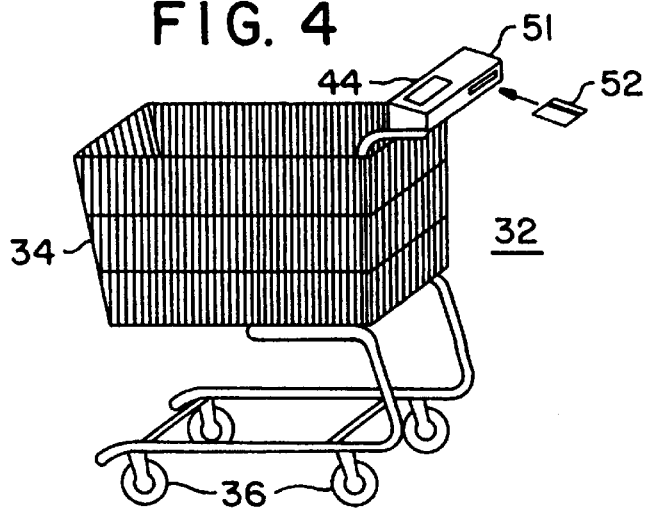
FIG. 4 is a preferred nutritional database access and information system on board a shopping cart the location of which is indicated in phantom.

FIG. 4 is a mobile apparatus 32 for generating personalized nutritional data information in accordance with the present invention. The apparatus in one embodiment comprises a mobile base 34 supported by a plurality of wheels 36, and may comprise a shopping cart. Referring to FIG. 4A the mobile base 34 further supports means 38 for inputting personal data relating to an individual. In a preferred embodiment, means 38 comprises a magnetic card reader 51 and card 52. This embodiment also includes means 40 for inputting data identifying the food products which the individual intends to purchase or consume. Means 40, in a preferred embodiment comprises a bar code entry system. In the mobile system, processor means 42 is under the control of a prestored computer program stored in RAM 43. Output means 44 may comprise an LED or LCD display. Output means 44 may alternatively comprise a CRT display located separate from the cart and/or a telephonic communication line. After the applicable data is input onto the cart, the information may be read into the central system.

The on-cart unit of FIG. 4 will preferably include a bar-code scanner allowing entry of personal and product information by scanning a readable user ID card and bar codes of packaged food. This permits quick access to the NDB, and bypasses the need to enter basic level user information each time the NDB is accessed.

All of the above discussed systems utilize a relational nutritional database (NDB). This large database, stored in a RAM, will contain a listing of foods, the UPC bar-code number for prepackaged food products, and nutritional information regarding those foods. The NDB may include information such as the nutrient content of individual foods, allergy warnings, pesticide levels, and the names of individual stores which carry foods. NDB may also be stored on a large storage medium such as a CD-ROM.

In a supermarket setting, the embodiments of FIGS. 3 and 4 provide supermarket food shoppers with the ability to obtain individualized nutritional information while they shop, thereby allowing them to make better informed food choices.

For example, a shopper could find out quickly which of ten breakfast cereals best meets his or her nutritional goals, without the need to read and understand confusing nutrition labels. At the end of a shopping trip, the nutritional content of the total food purchase could be tabulated and nutritional feedback provided.

Figure 2:
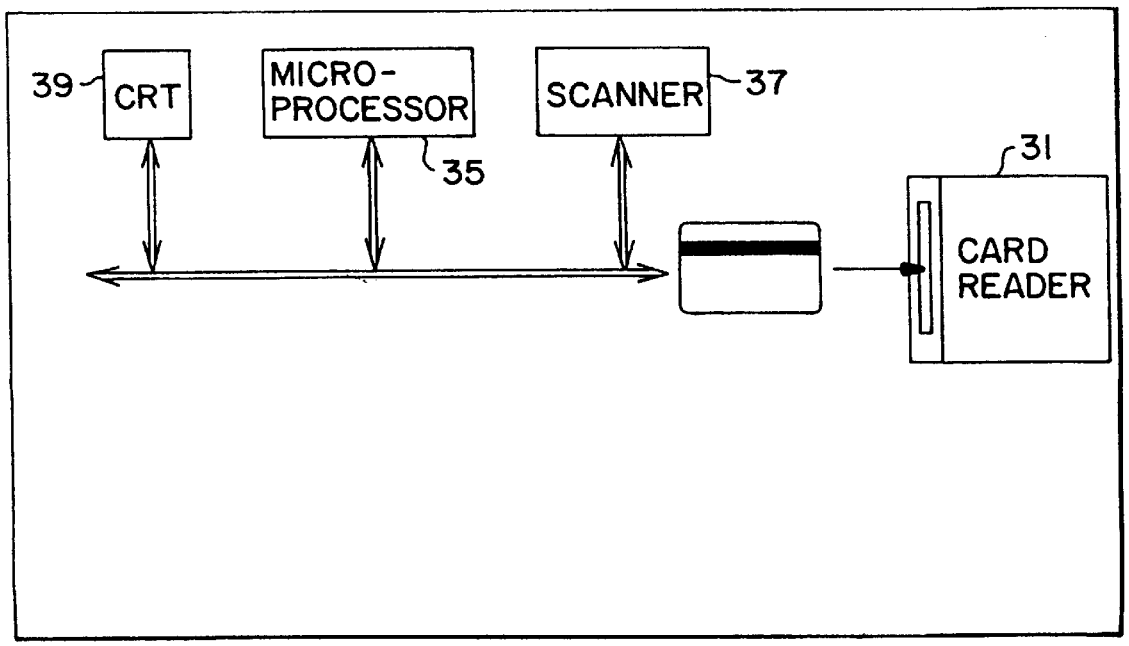
FIG. 2 is a block diagram of an individual data input system.

An individual could be provided with a personalized ID card readable by the system. A separate kiosk, such as shown in block diagram in FIG. 2, could be provided for the creation of a personalized account and system ID card. Such a kiosk would include a card entry slot 31, a microprocessor 35 and a barcode entry device 37. The user could be prompted by information appearing on a CRT display 39. Data such as the age, weight, height and medical conditions, et cetera would be entered once at the kiosk.

A magnetic card could also be prepared for the individual at the offices of participating doctors or nutritionists, thus allowing professional input into consumer food purchasing decisions. In such a situation, the participating doctor or nutritionist may have a portable or desktop version of the system shown in FIG. 2.

After the card was created, data such as the age, weight, height and medical condition, etc, could be called up automatically by the card. Such data could then be processed and then nutrition information provided. The present invention affords the consumer with the ability to make informed food choices so as to avoid guesswork.

In yet a further embodiment, a system for providing personalized nutritional information could also be provided for purchases at the check-out counter. Information could be based on single food items, or on weekly food purchases. The processor within the checkout register would act as a terminal. User input is limited to entry of a personalized code, directing the processor to provide information tailored to the consumer. Output would be in the form of a printed report received at the time of purchase. A consumer could enter a code number for specialized reports, or a default program could be run. Based on the number of days of consumption, limited dietary assessment of nutrient intake could be provided on large food purchases. Alternatively, feedback could be given regarding whether the consumer successfully purchased the foods which they were targeting. Items having a high fat or high cholesterol content could be flagged.

Another feature of the present invention is that it provides the ability to monitor the patterns of food purchase behavior over a wide area, which could be used for nutritional research purposes. It could provide feedback and training to consumers trying to make better food choices. Alternative choices or a composite profile of those foods purchased on a particular shopping trip could be listed.

Figure 5:
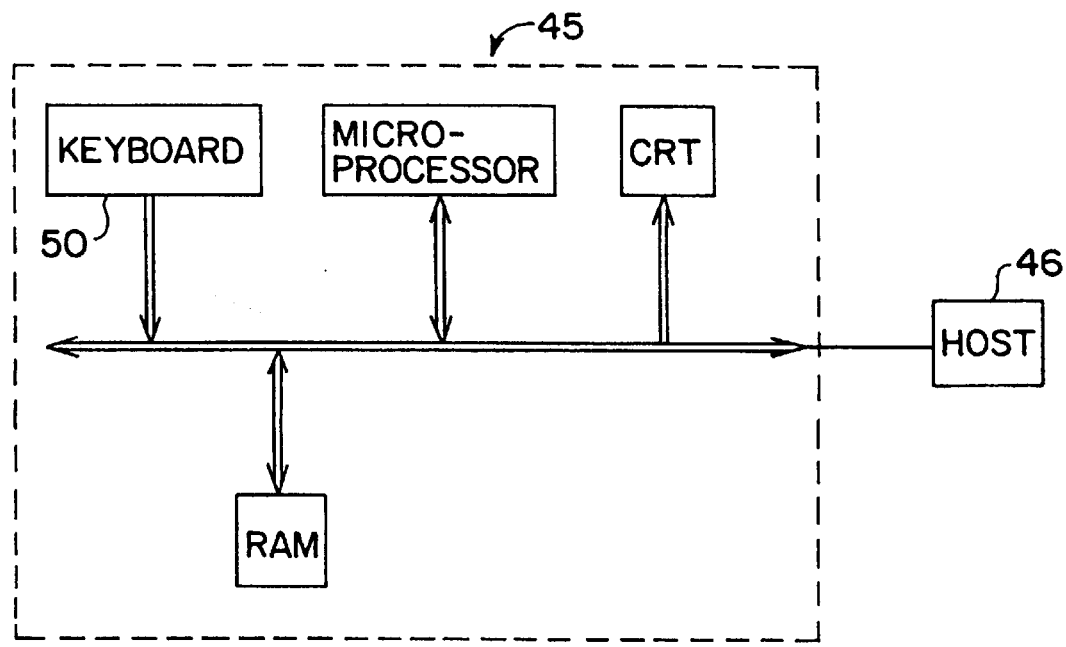
FIG. 5 is a block diagram of a preferred nutritional database access and information system comprising a home computer linked to a remote host computer.

Referring to FIG. 5, a home based PC base communication system is disclosed. The unit is comprised of a personal computer 45 situated at the user's site. The computer communicates with a host computer system 46 via a modem. Product choice information would be input via a keyboard 50 or graphical user interface. The host unit would store the main control program and NDB, and transmit processed data based upon the individual's food choices. Personal user ID data could be kept under an account number or entered separately.

In yet a further embodiment, the system comprises a 900 number phone system. This unit functions similar to the home base PC system. In this case, access to the NDB is gained through a 900 phone system. The user's telephone would provide access to a voice menu system, which would be linked to the remote host unit. Output could be in the form of voice output or mailed reports. This system would feature fast, easily accessible nutrition information on a food-by-food basis provided over phone lines.

The present invention has been described with reference to the above detailed description. It is to be appreciated that other embodiments will fulfill the spirit and scope of the present invention and that the true nature and scope of the present invention is to be determined with reference to the claims appended hereto.

I claim:

1. Apparatus for generating personalized nutritional information for a shopper or shoppers comprising:
    (a) means for inputting personal data relating to an individual;
    (b) barcode means for inputting data identifying at least one food product which said shopper has selected or specified, or has purchased or consumed;
    (c) processor means under the control of a prestored computer program for correlating the personal data with prestored nutritional data, including a barcode address, pertinent to the at least one food product which said shopper has selected or specified, or has purchased or consumed; and
    (d) means for outputting information to said shopper at the point of food purchase, or at their home or other location away from the point of the food purchase, pertinent to the at least one food product and the personal data of the individual.

2. The apparatus of claim 1 wherein said means for outputting information to said shopper based on the at least food product and the personal data of the individual comprises a CRT monitor.

3. The apparatus of claim 1 wherein said input personal data includes information pertinent to an individual's medical condition, height, weight, age, gender, nutritional preferences, demographic data or dietary regulated condition.

4. Apparatus for generating personalized nutritional information for a shopper or shoppers comprising:

(a) means for inputting personal data relating to an individual;

(b) barcode means for inputting data identifying at least one food product which said shopper has selected or specified, or has purchased or consumed;

(c) processor means under the control of a prestored computer program for correlating the said personal data with prestored nutritional data, including a barcode address, pertinent to the at least one food product which said shopper has selected or specified, or has purchased or consumed;

(d) means for outputting information to the shopper at the point of the food purchase, or at their home or other location away from the point of the food purchase, pertinent to the at least one food product and the personal data of the individual; and (e) a support housing.

5. The apparatus for generating personalized nutritional information of claim 4 wherein said support housing comprises a kiosk.

6. Apparatus for generating personalized nutritional information of claim 4 where said support housing comprises a check-out unit.

7. Apparatus for generating personalized nutritional information of claim 4 where said support housing comprises a hand-held unit.

8. The apparatus of claim 4 wherein said means for outputting personalized nutritional information to said shopper based on the at least one food product and the personal data of the individual comprises a printer.

9. The apparatus of claim 4 wherein said means for outputting personalized nutritional information to said shopper based on the at least one food product and the personal data of the individual comprises a CRT monitor.

10. The apparatus of claim 4 wherein said input personal data includes information pertinent to an individual's medical condition, height, weight, age, gender, nutritional preferences, demographic data or dietary regulated condition.

11. A method for providing a shopper or shoppers with personalized nutrition information regarding food purchased or consumed, or food selected or specified by a shopper or shoppers, comprising the following steps:

(a) inputting personal data relating to an individual;

(b) selecting or specifying at least one food product which said shopper is interested in, or has purchased or consumed, and inputting data identifying said food product;

(c) correlating the personal data with prestored nutritional data, including a barcode address, pertinent to the at least one food product which said shopper has specified or selected, or has purchased or consumed; and (d) outputting information at the point of the food purchase, or at the shopper's home or other location away from the point of the food purchase, pertinent to the at least one food product and the personal data of the individual.

12. Method of claim 11 where said output information consists of optional food choices.

13. Method of claim 11 where said output information consists of a recommendation for dietary improvement.

14. Method of claim 11 where said output information consists of a composite profile of purchased or consumed foods, or foods contemplated for purchase or consumption.

15. Method of claim 11 where said output information consists of an individual's nutrient intake status.

16. Method of claim 11 where said output information consists of an individual's food purchase pattern.

17. The method of claim 11 wherein said input personal data includes information pertinent to an individual's medical condition, height, weight, age, gender, nutritional preferences, demographic data or dietary regulated condition.

18. The method of claim 11 wherein said input personal data is input by means of a magnetically coded card.

19. The method of claim 11 wherein said input personal data is input by means of a barcode reader.

20. The method of claim 11 wherein said input personal data is input by means of a keypad entry device.

* * * * *